US011399892B2

(12) United States Patent
Yu et al.

(10) Patent No.: US 11,399,892 B2
(45) Date of Patent: Aug. 2, 2022

(54) SIDE-FIRE LASER FIBER HAVING A MOLDED REFLECTIVE SURFACE

(71) Applicant: Boston Scientific Scimed, Inc., Maple Grove, MN (US)

(72) Inventors: Honggang Yu, San Jose, CA (US); Rongwei Jason Xuan, Fremont, CA (US); Jian James Zhang, Santa Clara, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 601 days.

(21) Appl. No.: 15/558,572

(22) PCT Filed: Mar. 19, 2015

(86) PCT No.: PCT/US2015/021415
§ 371 (c)(1),
(2) Date: Sep. 15, 2017

(87) PCT Pub. No.: WO2016/148718
PCT Pub. Date: Sep. 22, 2016

(65) Prior Publication Data
US 2018/0049806 A1    Feb. 22, 2018

(51) Int. Cl.
*A61B 18/20* (2006.01)
*A61B 18/22* (2006.01)
(Continued)

(52) U.S. Cl.
CPC ............ *A61B 18/22* (2013.01); *A61B 18/245* (2013.01); *A61B 2018/00029* (2013.01); *A61B 2018/00511* (2013.01); *A61B 2018/00517* (2013.01); *A61B 2018/00577* (2013.01); *A61B 2018/00791* (2013.01); *A61B 2018/00898* (2013.01); *A61B 2018/225* (2013.01); *A61B 2018/2222* (2013.01); *A61B 2018/2238* (2013.01); *A61B 2018/2272* (2013.01); *A61B 2218/002* (2013.01)

(58) Field of Classification Search
None
See application file for complete search history.

(56) References Cited

U.S. PATENT DOCUMENTS 4,917,084 A * 4/1990 Sinofsky ................ A61B 18/24
606/15
5,000,752 A * 3/1991 Hoskin ................ A61B 18/203
606/9
(Continued)

FOREIGN PATENT DOCUMENTS

CN        2824861 Y    10/2006
CN       201179111 Y    1/2009
(Continued)

*Primary Examiner* — Lynsey C Eiseman
(74) *Attorney, Agent, or Firm* — Bookoff McAndrews, PLLC

(57) ABSTRACT

A side-fire laser fiber includes an optical fiber having a distal end and a fiber cap. The fiber cap is coupled to the distal end of the optical fiber and includes a molded reflective surface and a sealed cavity. The molded reflective surface defines a wall of the cavity. Laser energy discharged from the distal end along a central axis of the optical fiber is reflected off the molded reflective surface in a direction that is transverse to the central axis.

20 Claims, 9 Drawing Sheets

(51) Int. Cl.
*A61B 18/00* (2006.01)
*A61B 18/24* (2006.01)

(56) References Cited

U.S. PATENT DOCUMENTS

| | | |
|---|---|---|
| 5,366,456 A | 11/1994 | Rink et al. |
| 5,437,660 A | 8/1995 | Johnson et al. |
| 5,537,499 A | 7/1996 | Brekke |
| 5,836,941 A | 11/1998 | Masaya et al. |
| 7,909,817 B2 | 3/2011 | Griffin et al. |
| 9,618,700 B1* | 4/2017 | Griffin .................... G02B 6/32 |
| 2004/0059399 A1 | 3/2004 | Neuberger |
| 2005/0131399 A1 | 6/2005 | Loeb et al. |
| 2008/0108867 A1* | 5/2008 | Zhou .................... A61B 8/4483 |
| | | 600/104 |
| 2009/0287199 A1 | 11/2009 | Hanley et al. |
| 2011/0282330 A1* | 11/2011 | Harschack ............ A61B 18/24 |
| | | 606/3 |
| 2014/0121655 A1 | 5/2014 | Chia et al. |
| 2014/0249407 A1 | 9/2014 | Adler et al. |

FOREIGN PATENT DOCUMENTS

| | | |
|---|---|---|
| CN | 101623211 A | 1/2010 |
| EP | 0610991 A2 | 8/1994 |

* cited by examiner

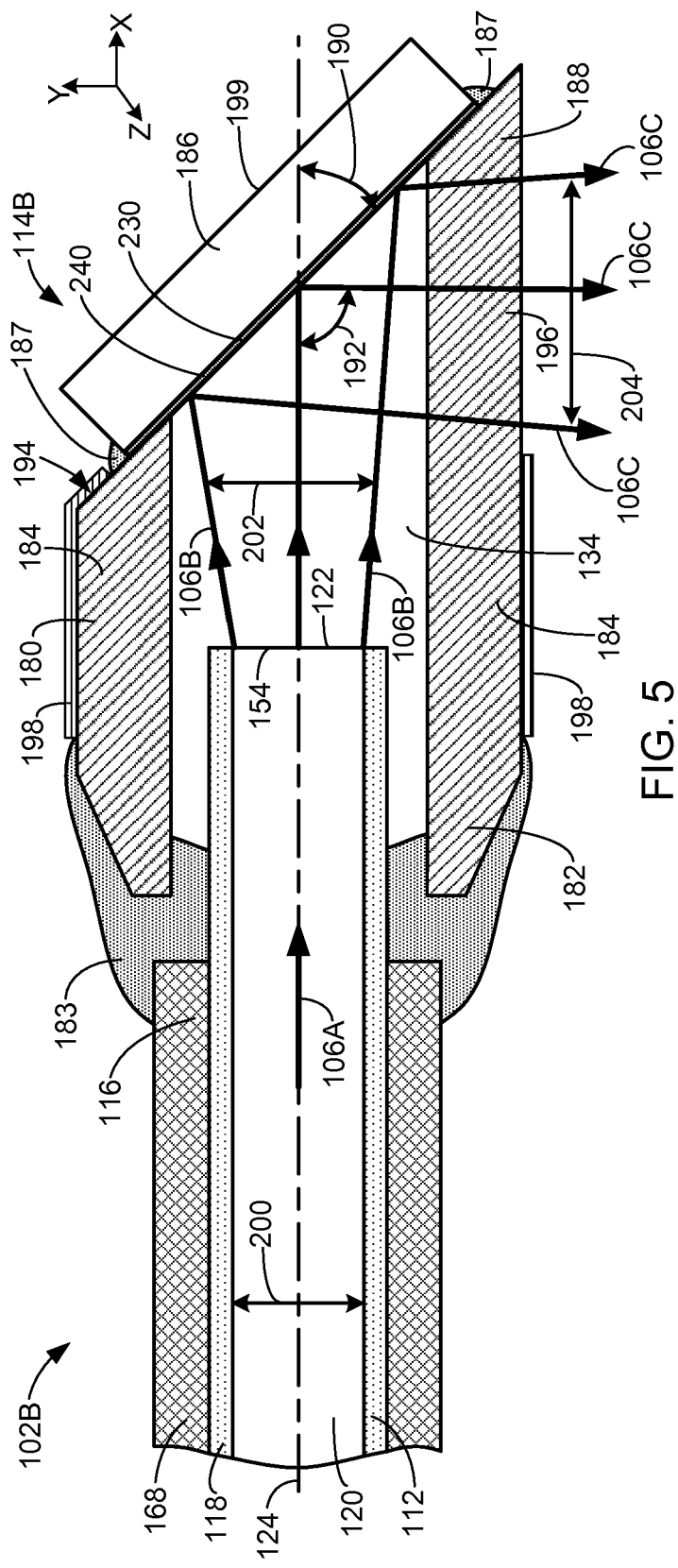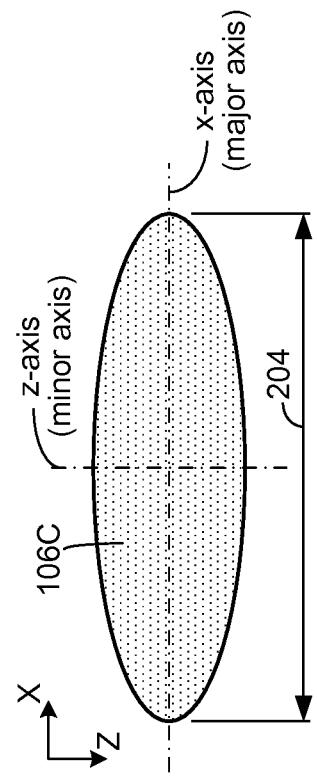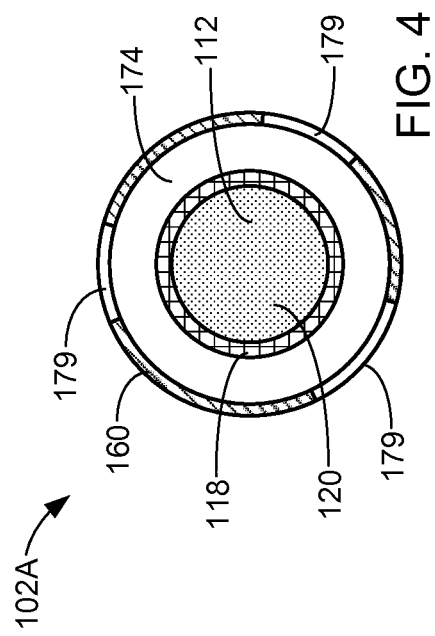

SIDE-FIRE LASER FIBER HAVING A MOLDED REFLECTIVE SURFACE

CROSS-REFERENCE TO RELATED APPLICATIONS

This application is the U.S. national phase entry under 35 U.S.C. § 371 of International Application No. PCT/US2015/021415, filed on Mar. 19, 2015.

FIELD

Embodiments of the invention are directed to a side-fire laser fiber for use in medical laser systems to deliver laser energy for a laser treatment and, more specifically, to a side-fire laser fiber having a molded reflective surface.

BACKGROUND

Medical laser systems have been used in various practice areas, such as, for example, urology, neurology, otorhinolaryngology, general anesthetic ophthalmology, dentistry, gastroenterology, cardiology, gynecology, and thoracic and orthopedic practices. Generally, these procedures require precisely controlled delivery of laser energy as part of the treatment protocol.

Medical laser systems are used to generate the desired laser energy and deliver it to targeted tissue or object through a laser fiber to perform a laser treatment on a patient. The laser fiber generally includes an optical fiber and a fiber cap over a distal end of the optical fiber. The laser source generates the laser energy that is transmitted through the optical fiber and is discharged through the fiber cap to the targeted tissue or object. The laser energy may be discharged along a central axis of the optical fiber and through an end of the fiber cap (end-fire laser fiber), or the laser energy may be discharged laterally from the fiber cap relative to the central axis (side-fire laser fiber).

FIG. 13 is a side cross-sectional view of an exemplary side-fire laser fiber 300 in accordance with the prior art, which is similar to that described in U.S. Pat. No. 7,909,817 issued to AMS Research Corporation, which is incorporated by reference herein in its entirety.

The laser fiber 300 includes an optical fiber 302 and a fiber cap 304 that is attached to a distal end of the optical fiber 302. An adhesive 306 may be used to attach a proximal end of the fiber cap 304 to the optical fiber 302. A core 308 of the optical fiber 302 (which is typically silica), through which laser energy 310 is transmitted along a central or longitudinal axis 312, may be fused to the fiber cap 304 at locations 314 and 316.

A beveled terminating end surface 320 is formed at the distal end of the core 308. An air cavity 322 surrounds the surface 320 to promote total internal reflection of laser energy 310 off the surface 320. As a result, laser energy 310 transmitted through the core 308 is reflected off the beveled surface 320 laterally relative to the central axis 312.

A metal cap 324 having a side port 326, through which the laser energy 310 is discharged, may be used to protect the distal end of the laser fiber 300. A fluid may be fed through fluid channels 328 between the metal cap 324 and the fiber cap 304 to cool the fiber cap 304.

The performance of a laser treatment on a patient often requires the precise delivery of the laser energy to the targeted tissue or object. The beveled surface 320 is conventionally formed by mechanically polishing the distal end surface of the core 308. However, the surface 320 can be deformed as a result of the fusion of the core 308 to the fiber cap 304 at the locations 314 and 316, for example. The resultant deformities 330 result in a non-uniform surface 320, which can scatter the laser energy 310A and 310B that impacts the deformed areas 330 of the surface 320, as indicated by arrows 332. This scattering of the laser energy at the surface 320 can lead to an irregular output laser beam that is delivered to the targeted tissue or object, thereby potentially adversely affecting laser treatments performed using the laser fiber 300. The scattered laser energy may also cause damage to the laser fiber 300.

There is a continuous need for improvements in laser fiber probes/fiber caps, such as improvements that reduce manufacturing costs and increase reliability. Embodiments described herein provide solutions to these and other problems, and offer other advantages over the prior art.

SUMMARY

Embodiments of the invention are directed to a side-fire laser fiber that is configured for use with medical laser systems to discharge laser energy laterally relative to a central/longitudinal axis of the laser fiber. In some embodiments, the side-fire laser fiber includes an optical fiber and a fiber cap. The fiber cap is coupled to a distal end of the optical fiber and includes a molded reflective surface and a sealed cavity. The molded reflective surface defines a wall of the cavity. Laser energy discharged from the distal end along a central axis of the optical fiber is reflected off the molded reflective surface in a direction that is transverse to the central axis.

In some embodiments, the laser energy discharged from the distal end of the optical fiber has a cross-sectional area, measured in a plane that is perpendicular to the central axis that expands with distance from the distal end of the optical fiber along the central axis.

In some embodiments, the reflective surface is curved in a plane extending parallel to the central axis. In some embodiments, the reflective surface is curved in a plane extending perpendicularly to the central axis.

In some embodiments, an exterior side of the molded reflective surface defines a wall of the cavity, and an internal side of the molded reflective surface reflects laser energy discharged from the optical fiber in a direction that is transverse to the central axis. In some embodiments, the cavity is located distally of the distal end of the optical fiber and the molded reflective surface. In some embodiments, the fiber cap includes a main body and a cover member. The main body defines the molded reflective surface and an opening to the cavity. The cover member is attached to the main body and seals the opening.

In some embodiments, the laser fiber includes a metal cap having a proximal end attached to the distal end of the optical fiber. At least a portion of the fiber cap is received within a distal end of the metal cap. In some embodiments, the distal end of the metal cap includes a side port in a wall of the metal cap through which the laser energy is discharged. In some embodiments, the laser fiber includes fluid conduit and fluid channels between the metal cap and the fiber cap, and the optical fiber is within the fluid conduit. Fluid delivered through the fluid conduit travels through the fluid channels and out the side port of the metal cap.

In some embodiments, a portion of the cavity extends between the distal end of the optical fiber and the molded reflective surface. In some embodiments, the fiber cap includes a main body having a proximal end that is attached to the optical fiber and a distal end having an opening to the cavity. A cover member is attached to the main body and seals the cavity and supports the molded reflective surface. In some embodiments, the main body includes a distal surface that is oriented at an oblique angle to the central axis, and the cover member is attached to the distal surface. In some embodiments, the molded reflective surface is approximately oriented at the oblique angle to the central axis.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

Preferred features of the embodiments of the present invention are disclosed in the accompanying drawings, wherein similar reference characters denote similar elements throughout the several views, wherein the drawings are not drawn to scale and wherein:

FIG. 4 is a front cross-sectional view of a portion of the side-fire laser fiber of FIG. 3 taken along line 4-4.

FIG. 5 is a side cross-sectional view of an exemplary side-fire laser fiber in accordance with embodiments of the invention.

FIG. 5A depicts the profile of the discharged laser beam from the side-fire laser fiber depicted in FIG. 5.

DETAILED DESCRIPTION OF ILLUSTRATIVE EMBODIMENTS

Figure 1:
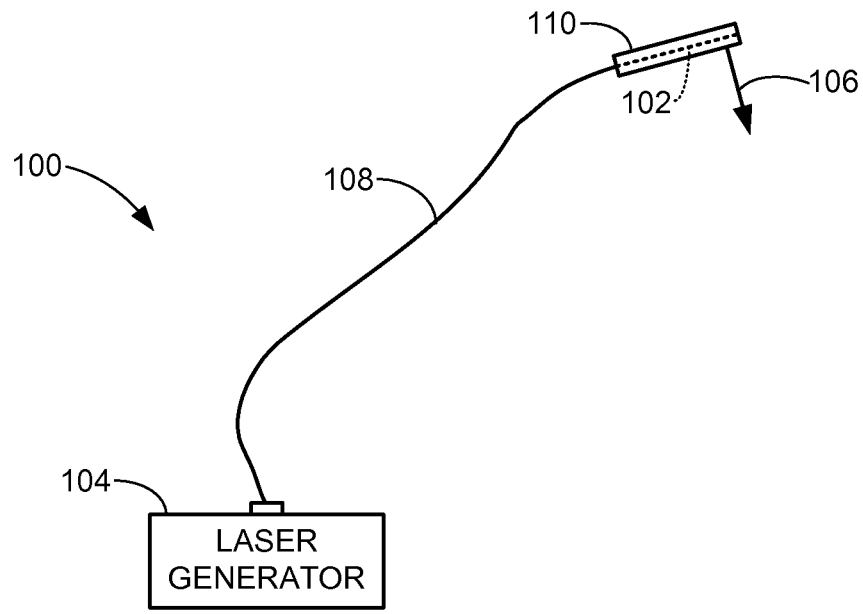
FIG. 1 is a schematic diagram of an exemplary surgical laser system in accordance with embodiments of the invention.

Embodiments of the invention are described more fully hereinafter with reference to the accompanying drawings. Elements that are identified using the same or similar reference characters refer to the same or similar elements. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic diagram of an exemplary medical laser system 100, which includes a side-fire laser fiber 102 in accordance with one or more embodiments of the invention. In some embodiments, the system 100 comprises a laser generator 104 that generates laser energy 106, which is optically coupled to the laser fiber 102 through a waveguide 108 (e.g., an optical fiber). Laser energy 106 generated by the laser generator 104 is transmitted through the waveguide 108 to the laser fiber 102, which discharges the laser energy 106 to perform a desired medical laser procedure, such as tissue ablation, or urinary or kidney stone fragmentation, for example.

In some embodiments, the system 100 includes a probe 110, such as an endoscope, in which at least a distal end of the laser fiber 102 is supported, as shown in FIG. 1. In some embodiments, fluid is delivered to the laser fiber through the probe 110 to cool the distal end of the laser fiber 102, and to prevent debris from sticking to the laser fiber 102, for example.

In some embodiments, the laser generator 104 comprises one or more conventional laser sources, such as laser resonators, that produce the laser energy 106 having desired properties. In some embodiments, the system 100 produces the laser energy 106 in the form of a pulse train or continuous wave. In some embodiments, the laser generator 102 includes Q-switched laser rods to produce the laser energy 106, such as, for example, a holmium doped yttrium aluminium garnet (Ho:YAG) laser rod, a thulium doped yttrium aluminium garnet (Tm:YAG) laser rod, or other conventional laser rod suitable for producing the desired laser energy 106. In some embodiments, the laser energy 106 has a power of approximately 1-50 W, a pulse repetition frequency of 1-2000 Hz, and an energy level of 1 mJ-5 J. Laser energies 106 having other parameters may also be used.

Figure 2:
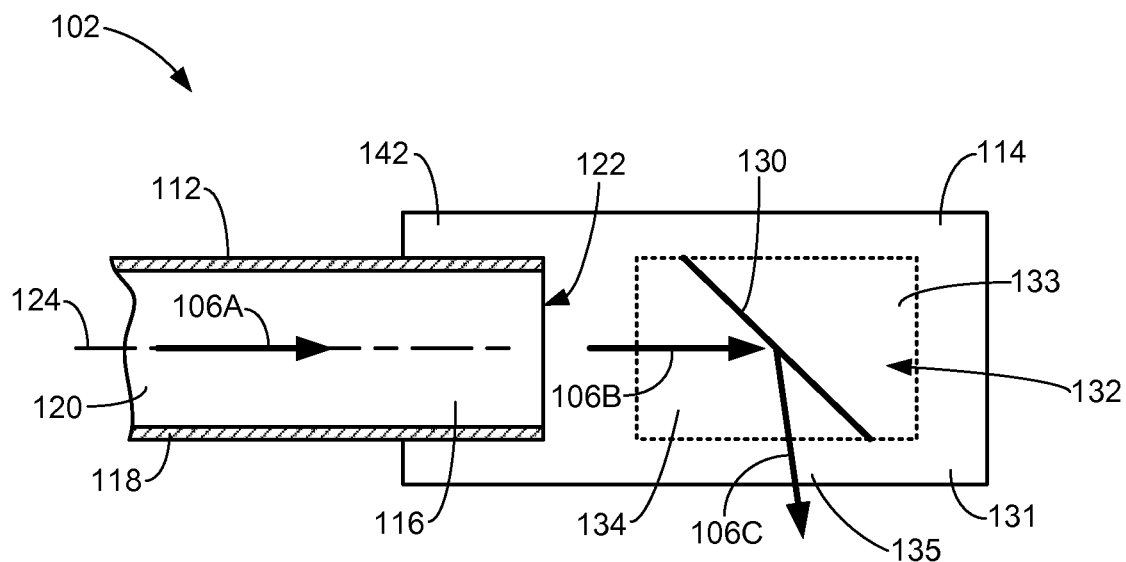
FIG. 2 is a simplified diagram of an exemplary side-fire laser fiber in accordance with embodiments of the invention.

FIG. 2 is a simplified diagram of an exemplary side-fire laser fiber 102 in accordance with embodiments of the invention. In some embodiments, the laser fiber 102 includes an optical fiber 112 and a fiber cap 114 coupled to a distal end 116 of the optical fiber 112. In some embodiments, the optical fiber 112 includes cladding 118 that surrounds a core 120, through which the laser energy 106 is transmitted. In some embodiments, portions of the cladding 118 may be removed from the distal end 116 of the core 120. In some embodiments, the core 120 has a terminating end surface 122. In some embodiments, the end surface 122 is oriented perpendicularly to a central axis 124 of the optical fiber 112 or the core 120, as shown in FIG. 2.

In some embodiments, the fiber cap 114 is formed of one or more biocompatible materials such as, for example, glass, biocompatible adhesive, and/or other biocompatible materials. In some embodiments, the fiber cap 114 is cylindrical and is generally coaxial to the central axis 124 of the optical fiber. In some embodiments, the fiber cap 114 includes a molded reflective surface 130 that is formed through a molding process, such as injection molding or cast molding, for example. In some embodiments, the molded reflective surface 130 is an integral component of a molded cap body 131.

In some embodiments, the molded reflective surface 130 defines a wall of a cavity, generally referred to as 132. In some embodiments, the cavity 132 is sealed and is filled with air.

In some embodiments, the cavity 132 of the fiber cap 114 is in the form of a sealed cavity 133 that is located distally from the surface 130, as shown in FIG. 2. In some embodiments, the cavity 133 promotes total internal reflection of the laser energy 106 off the molded surface 130. In an alternative embodiment, the fiber cap 114 includes a cavity 134 that is located on a proximal side of the surface 130 between the surface 130 and the end surface 122 of the optical fiber 112.

The laser energy 106 produced by the laser generator 104 is transmitted along a central axis 124 of the optical fiber 112 (laser energy 106A), discharged through the terminating end surface 122 of the optical fiber 112 (laser energy 106B), and then reflected off the molded reflective surface 130 in a direction that is transverse to the central axis 124 (laser energy 106C), as shown in FIG. 2. In some embodiments, the laser energy 106C is discharged through a wall 135 of the fiber cap 114.

In some embodiments, the reflective surface 130 provides a uniform surface for reflecting the laser energy 106 laterally relative to the central axis 124. This uniformity to the reflective surface 130 is maintained through the assembly of the laser fiber 102. Specifically, in some embodiments, the fiber cap 114 is not fused to the optical fiber 112 in a manner that deforms the reflective surface 130 and produces irregularities in the laser energy 106 reflected from the reflective surface 130, as can be the case in prior art laser fibers. Additionally, the molding of the reflective surface 130 allows for flexibility as to the shape of the surface 130 to customize the profile or shape of the discharged laser energy 106C (laser beam) as discussed below. In some embodiments, the molded reflective surface 130 can be a binary diffraction optical surface that is configured to shape the discharged laser energy 106C into a desired beam profile (circular, donut shaped, line shape, split beams, etc.).

Figure 3:
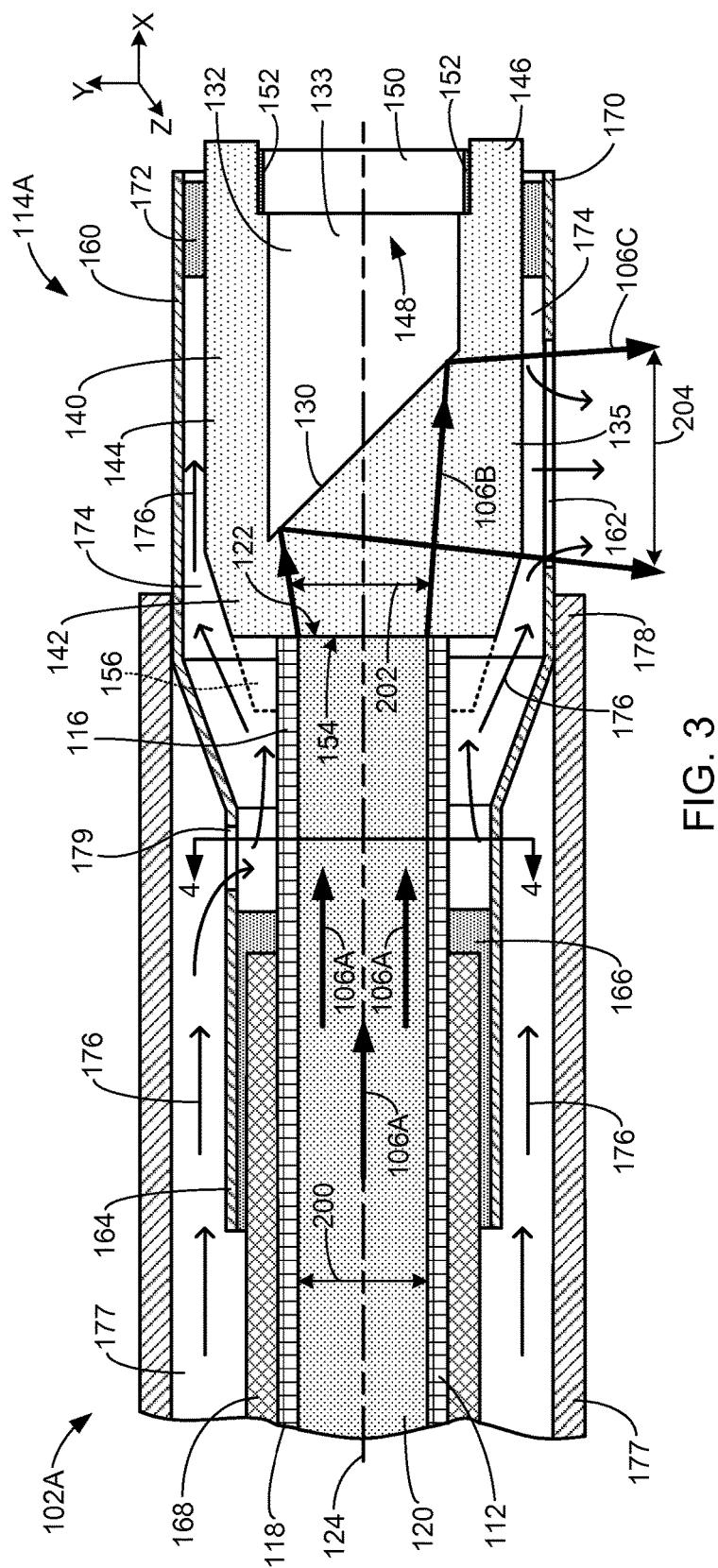
FIG. 3 is a side cross-sectional view of an exemplary side-fire laser fiber in accordance with embodiments of the invention.

FIG. 3 is a side cross-sectional view of an exemplary side-fire laser fiber 102A formed in accordance with embodiments of the invention, and FIG. 4 is a front cross-sectional view of a portion of the side-fire laser fiber 102A of FIG. 3 taken generally along line 4-4. In some embodiments, the fiber cap 114A of the laser fiber 102A includes a cap body 140 that is either partially or entirely formed through a molding process. In some embodiments, the cap body 140 is formed of glass or other suitable biocompatible material. In some embodiments, the cap body 140 is a cylindrical body that is substantially coaxial with the central axis 124, which is aligned with the X-axis of the X-Y-Z coordinate system depicted in the figure.

In some embodiments, the cap body 140 includes the molded reflective surface 130 at a proximal end 142, which forms a wall of the cavity 133. In some embodiments, the cap body 140 defines one or more side walls 144 of the cavity 133 that extend from the molded reflective surface 130 to a distal end 146. In some embodiments, the one or more side walls 144 are formed through the molding process that formed the molded reflective surface 130.

In some embodiments, the cap body 140 includes an opening 148 between the side walls 144 at the distal end 146 of the cap body 140. In some embodiments, a cover member 150 formed of one or more biocompatible materials covers the opening 148 and seals the cavity 133. In some embodiments, the cover member 150 is secured to the distal end 146 of the cap body 140 using a suitable biocompatible adhesive 152, or other suitable fastening technique.

In some embodiments, the cap body 140 includes a proximal surface 154 that is located adjacent to or abuts the terminating surface 122 of the optical fiber 112 or the core 120. In some embodiments, the surface 154 is fused to the surface 122 of the core 120, or the surface 122 of the core 120 and the cladding 118. The fusion of the surface 122 to the surface 154 may be performed using an electrical arc fusion splicer, filament fusion splicer, or a $CO_2$ laser, for example. Other fusing methods may be used as will be understood by those of ordinary skill in the art.

In some embodiments, the cap body 140 includes a cylindrical socket 156 (shown in phantom lines) that receives the distal end 116 of the optical fiber 112, and assists in aligning the terminating surface 122 of the optical fiber 112 with the proximal surface 154 of the cap body 140. In some embodiments, an adhesive is used to bond the interior walls of the socket 156 to the exterior surface of the optical fiber 112, which can either include cladding 118 or can be stripped of the cladding 118 such that the core 120 contacts the interior walls of the socket 156.

As mentioned above, the air-filled cavity 133 promotes total internal reflection of the laser energy 106 off the molded reflective surface 130. As a result, the laser energy 106A transmitted through the core 120 along the central axis 124 is discharged from the surface 122 as laser energy 106B, which is reflected off the internal side of the molded reflective surface 130 due to total internal reflection and discharged as laser energy 106C through a wall or portion 135 of the cap body 140 to a desired target, as shown in FIG. 3.

In some embodiments, the laser fiber 102A includes a metal cap 160 that protects the fiber cap 114A from damage from normal use of the laser fiber 102A. In some embodiments, the metal cap 160 includes a side port 162, through which the laser energy 106C is discharged.

In some embodiments, the metal cap has a proximal end 164 that is attached to the distal end 116 of the optical fiber 112 using an adhesive 166 or other suitable fastening technique, as shown in FIG. 3. In some embodiments, the proximal end 164 is attached to a jacket 168 and/or the cladding 118 of the optical fiber 112. In some embodiments, a distal end 170 of the metal cap 160 is attached to the distal end 146 of the cap body 140 using a biocompatible adhesive 172, or other suitable fastening technique.

In some embodiments, fluid channels 174 are formed between the metal cap 160 and the fiber cap 114A. The fluid channels 174 are configured to receive a fluid flow, represented by arrows 176, that circulates around the fiber cap 114 to cool the fiber cap 114A or to irrigate the treatment area, for example. In some embodiments, the fluid flow 176 is discharged through the side port 162.

In some embodiments, the laser fiber 102A includes fluid conduit 177 for supplying the fluid flows 176. In some embodiments, the optical fiber 112 is within the fluid conduit 177. In some embodiments, the metal cap 160 is configured to seal a distal end 178 of the fluid conduit 177, as shown in FIG. 3. In some embodiments, the metal cap 160 includes openings 179, through which the fluid flow 176 enters the fluid channels 174, as shown in FIGS. 3 and 4.

FIG. 5 is a side cross-sectional view of an exemplary side-fire laser fiber 102B in accordance with embodiments of the invention. In some embodiments, the laser fiber 102B includes a fiber cap 114B comprising a main body 180, a reflective surface 230, and the cavity 134. In some embodiments, the cavity 134 extends between the distal end 116 of the optical fiber 112 and the reflective surface 230.

In some embodiments, the main body 180 is formed of glass. In some embodiments, the main body 180 is cylindrical and is substantially coaxial to the central axis 124. In some embodiments, the main body 180 has a proximal end 182 that is attached to the optical fiber 112 using a biocompatible adhesive 183, or other suitable fastening technique. In some embodiments, the main body includes side walls 184 that extend along the axis 124 and partially define the cavity 132.

In some embodiments, the reflective surface 230 is attached to, or formed integral with (molded), a cover member 186, and faces the end surface 122 of the optical fiber 112. In some embodiments, the reflective surface 230 includes a coating 240 that is highly reflective of the laser energy 106.

In some embodiments, the cover member 186 is attached to a distal end 188 of the main body 180 using a biocompatible adhesive 187, or other suitable fastening technique. In some embodiments, the cover member 186 seals the cavity 134. In some embodiments, the cover member 186 is attached to the main body 180 at an oblique angle 190 relative to the central axis 124. The angle 190 at least partially determines the discharge angle 192, at which the laser energy 106C is discharged from the fiber cap 114B relative to the central axis 124.

Figure 6:
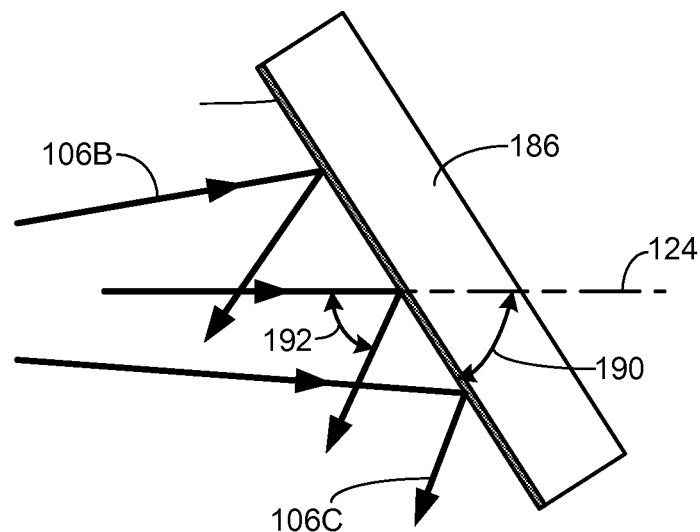
FIGS. 6 and 7 are simplified side views of a portion of a fiber cap illustrating exemplary angles at which the cover member may be supported, in accordance with embodiments of the invention.
Figure 7:
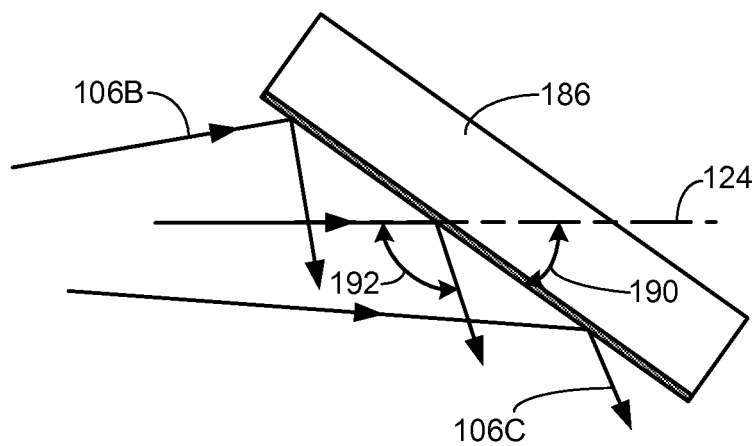

FIGS. 6 and 7 are simplified side views of the cover member 186 illustrating exemplary angles 190, in which the cover member 186 may be supported. Larger angles 190 may result in an acute discharge angle 192 relative to the central axis 124, as shown in FIG. 6. As the angle 190 is reduced from that illustrated in FIG. 6, the discharge angle 192 increases to approximately 90 degrees, as shown in FIG. 5, or to an obtuse angle, as shown in FIG. 7. As a result, one may customize the angle 192 at which the laser energy 106C is discharged by adjusting the angle at which the cover member 186 is attached to the main body 180.

In some embodiments, the main body 180 includes a distal surface 194 at the distal end 188 that is oriented at an oblique angle to the central axis 124, as shown in FIG. 5. In some embodiments, the cover member 186 is attached to the surface 194 to set the angle 190 of the cover member 186 and the molded reflective surface 130 relative to the central axis 124 based on the angle of the distal surface 194.

In some embodiments, the laser energy 106C is discharged through a transmissive portion 196 of the main body 180. In some embodiments, portions of the exterior surface of the main body 180 that do not cover the transmissive portion 196 include a highly reflective coating 198 to prevent leakage of the laser energy 106 through those portions of the main body 180.

In some embodiments, the laser fiber 102B is configured to provide a temperature sensing function. In some embodiments, a surface 199 (FIG. 5) of the cover member 186 that is opposite the reflective surface 230 includes a coating of a biocompatible material that is configured to fluoresce in response to exposure to electromagnetic energy having a temperature sensing wavelength that is transmitted through the optical fiber 112. The temperature at the distal end 188 can be estimated by the system 100 based on the intensity of the fluorescence from the coated surface 199 that is reflected back through the optical fiber 112.

In some embodiments, the reflective coating 240 on the reflective surface 230 is transmissive to electromagnetic energy at the temperature sensing wavelength and highly reflective at the wavelength of the laser energy 106. For example, the coating 240 on the surface 230 may be highly reflective of electromagnetic energy having a wavelength of 532 nm, and highly transmissive of electromagnetic energy having a wavelength of approximately 420 nm. Thus, when laser energy 106 having a wavelength of approximately 532 nm is transmitted through the optical fiber 112, it is reflected off the surface 230 and discharged through transmissive portion 196 for use in a laser treatment. When a temperature sensing laser beam having a wavelength of approximately 420 nm is transmitted through the optical fiber 112, it passes through the coating 240 and surface 230 and contacts the coating on the surface 199, which responsively fluoresces at an intensity that is related to the temperature of the laser fiber 102B at the distal end 188. This fluorescence is reflected through the optical fiber 112 where it can be analyzed by the system 100 to estimate the temperature of the laser fiber 102B. For example, the temperature can be estimated by measuring the fluorescence signal decay time. This temperature sensing function can be used periodically or continually during a laser treatment to detect the temperature of at the distal end 188 of the laser fiber 102B. In some embodiments, the system 100 triggers an alarm signal when the sensed temperature exceeds a threshold temperature.

Figure 3A:
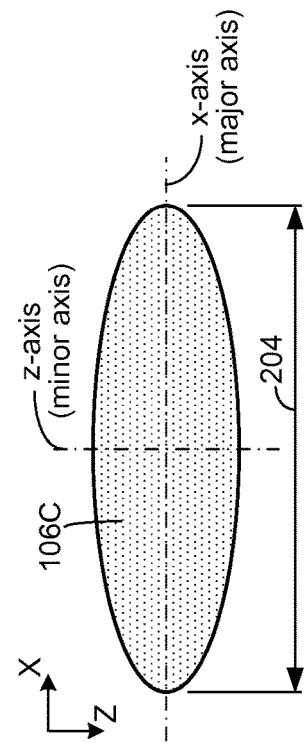
FIG. 3A depicts the profile of the discharged laser beam from the side-fire laser fiber depicted in FIG. 3.

Typically, the laser energy 106A has a circular profile and a diameter 200 that generally conforms to the diameter of the core 120 (see FIGS. 3 and 5). In some embodiments, the laser energy 106B has a diameter 202 or cross-sectional area, measured in a plane that is perpendicular to the central axis 124, which expands with distance from the surface 122 along the central axis 124, as shown in FIGS. 3 and 5. That is, for a flat, planar reflective surface 130, 230 as depicted in FIGS. 3 and 5 (i.e., a surface that is not curved as those depicted in FIGS. 8-11), discharged laser energy 106C generally has an elliptical beam profile where the major axis of the ellipse is aligned with the central axis 124 as depicted in FIGS. 3 and 5. In FIGS. 3 and 5, the major axis of the elliptical discharged laser beam, has a diameter identified as double-headed arrow 204. The beam profiles generated by the embodiments of the side-fire laser fibers depicted in FIGS. 3 and 5 are depicted in FIGS. 3A and 5A, respectively.

The expansion or divergence of the laser energy 106B is due to refraction from the change in medium from the glass core 120 of the optical fiber 112 to either the cap body 140 (FIG. 3) or the air chamber 134 (FIG. 5). Thus, in some embodiments, the portion of the cap body 140 between the surface 154 and the surface 130, 230, or the air chamber 133, 134, acts as a beam expander. The degree of beam expansion is determined, in part, by the distance between the terminating surface 122 of the optical fiber 112 and the molded reflective surface 130. This distance can be adjusted to provide the desired expansion of the laser energy 106A.

Figure 13:
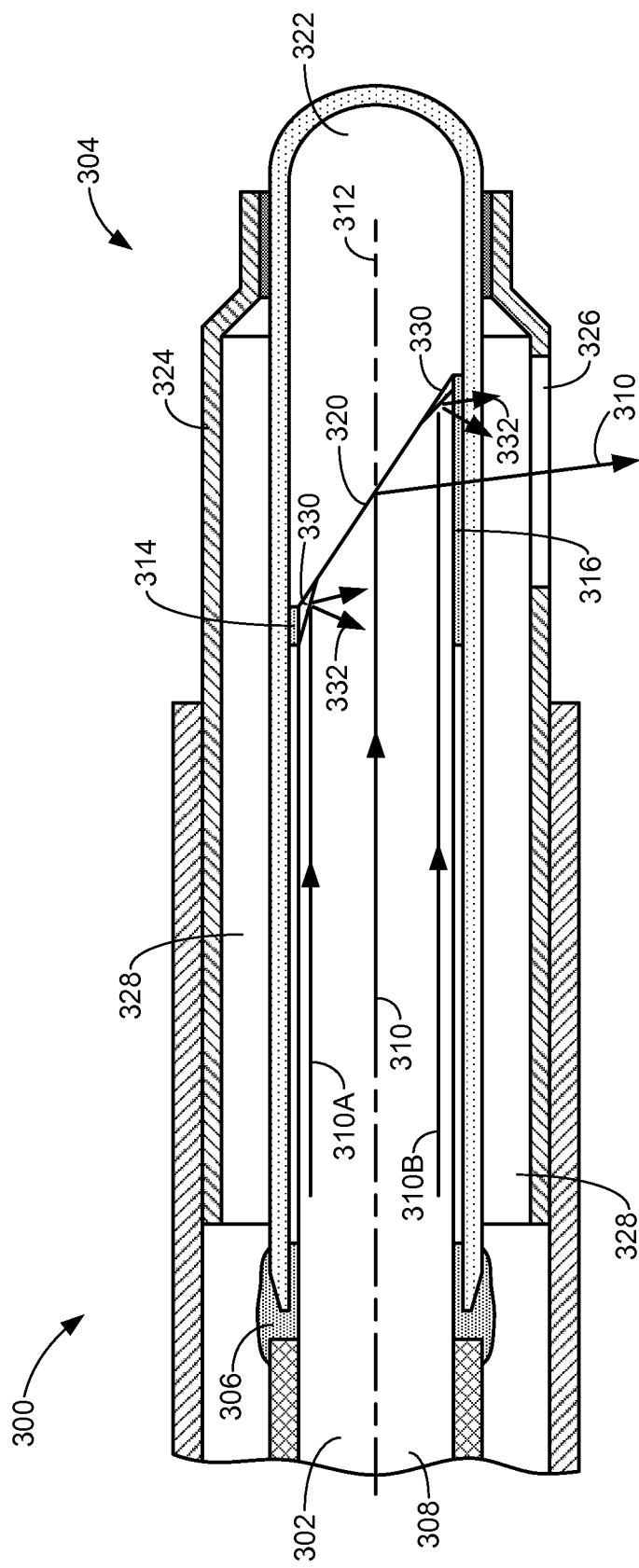
FIG. 13 is a simplified side cross-sectional view of a side-fire laser fiber in accordance with the prior art.

The expansion of the laser energy 106B discharged from the optical fiber 112 allows the laser fiber 102 to use optical fibers 112 having smaller diameter cores 120 than the optical fibers used in conventional laser fibers, such as that illustrated in FIG. 13, to produce an elliptical output beam 106C having a desired major axis diameter 204. For example, the laser fiber 102A may use an optical fiber 112 having a core diameter 200 of 500 µm to produce an elliptical output laser beam 106C having a major axis diameter 204 that is similar to the diameter of an output laser beam discharged from a conventional laser fiber using a 750 µm diameter optical fiber core. This can result in a substantial cost savings for the laser fiber 102 over the conventional laser fibers, as optical fibers having smaller cores cost less than optical fibers having larger cores.

As mentioned above, the molded reflective surface 130 may be in the form of a flat, planar surface (as depicted in FIGS. 3 and 5) that reflects the laser energy 106B at a desired angle. In some embodiments, the molded reflective surface 130 has a non-planar shape that reflects the laser energy 106B in a beam of laser energy 106C having a desired shape profile. Exemplary shapes for the molded reflective surface 130 will be described below with reference to FIGS. 8-11.

Figure 8A:
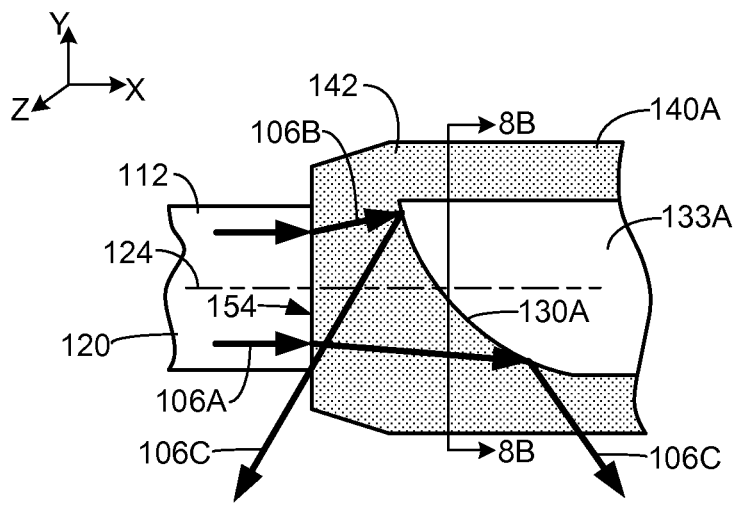
FIG. 8A is a simplified side cross-sectional view of a portion of a cap body in accordance with embodiments of the invention.
Figure 8B:
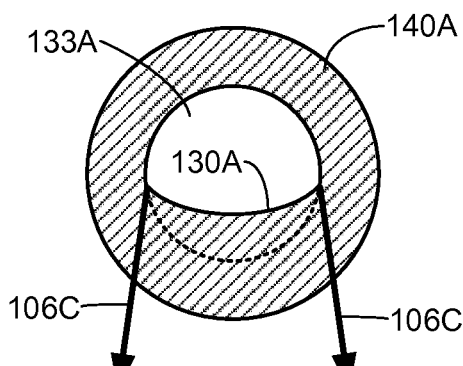
FIG. 8B is a front cross-sectional view of the cap body of FIG. 8A taken generally along line 8B-8B.
Figure 8C:
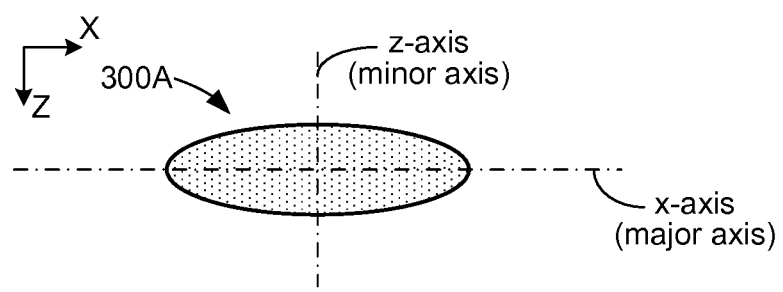
FIG. 8C depicts the beam profile generated by the cap body of FIGS. 8A and 8B.

FIG. 8A is a simplified side cross-sectional view of a portion of a cap body 140A and FIG. 8B is a front cross-sectional view of the cap body 140A of FIG. 8A taken generally along line 8B-8B, in accordance with embodiments of the invention. FIG. 8C depicts the beam profile 300A generated by the embodiment of the cap body 140A depicted in FIGS. 8A and 8B. The cap body 140A of FIGS. 8A and 8B includes a molded spherical plano concave reflective surface 130A. The molded spherical plano concave surface 130A expands or diverges the discharged laser energy 106C equally in 2 directions along the X and Z axes. Thus, the radius of curvature of the molded spherical plano concave (concave relative to the cavity 133A) reflective surface 130A of FIGS. 8A and 8B can be designed to control the degree that the discharged laser energy 106C expands or diverges in the X and Z directions such that the desired laser beam profile 300A size is achieved. In this embodiment, because, as discussed above, the laser energy 106B expands or diverges due to refraction from the change in medium from the glass fiber core 120 to the cap body 140A thereby resulting in the discharged laser energy 106C having an elliptical beam profile, the molded plano concave reflective surface 130A further expands the discharged laser energy 106C in the X and Z directions, resulting in a larger, elliptical beam profile 300A.

Figure 9A:
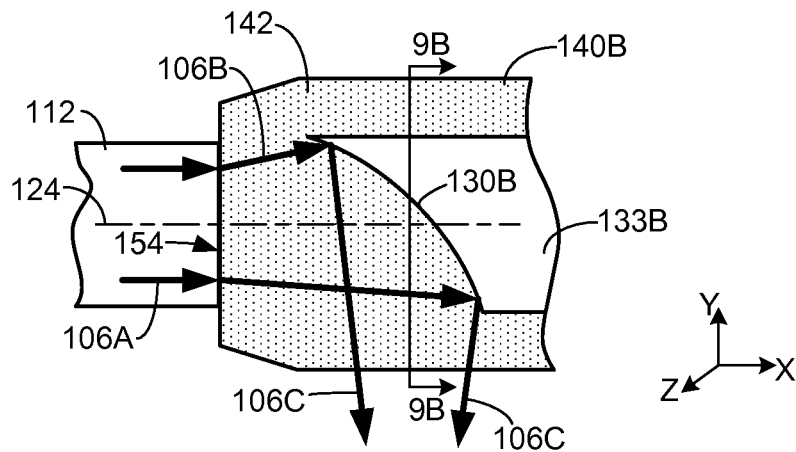
FIG. 9A is a simplified side cross-sectional view of a portion of a cap body in accordance with embodiments of the invention.
Figure 9B:
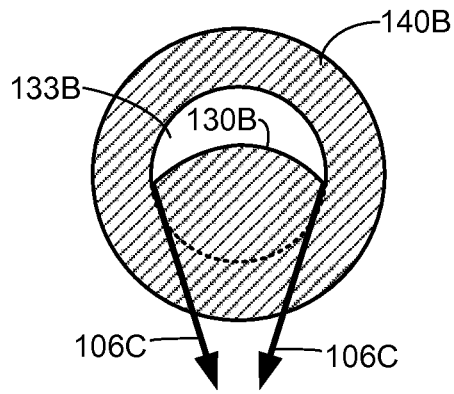
FIG. 9B is a front cross-sectional view of the cap body of FIG. 9A taken generally along line 9B-9B.
Figure 9C:
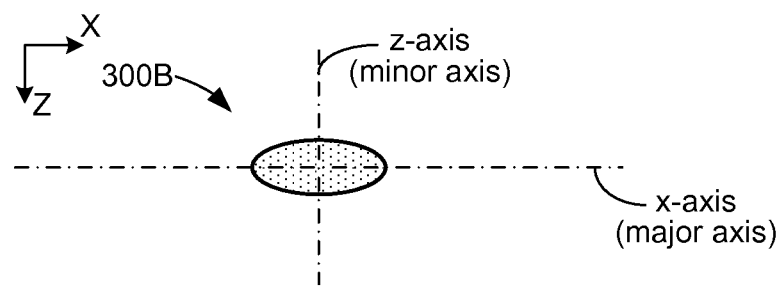
FIG. 9C depicts the beam profile generated by the cap body of FIGS. 9A and 9B.

FIG. 9A is a simplified side cross-sectional view of a portion of a cap body 140B and FIG. 9B is a front cross-sectional view of the cap body 140B of FIG. 9A taken generally along line 9B-9B, in accordance with embodiments of the invention. FIG. 9C depicts the beam profile 300B generated by the embodiment of the cap body 140B depicted in FIGS. 9A and 9B. The cap body 140B of FIGS. 9A and 9B includes a molded spherical plano convex reflective surface 130B. The molded spherical plano convex surface 130B focuses or converges the discharged laser energy 106C equally in 2 directions along the X and Z axes. Thus, the radius of curvature of the molded spherical plano convex (convex relative to the cavity 133B) reflective surface 130B of FIGS. 9A and 9B can be designed to control the degree that the discharged laser energy 106C is focused or converges in the X and Z directions such that the desired laser beam profile 300B size is achieved. In this embodiment, because, as discussed above, the laser energy 106B expands or diverges due to refraction from the change in medium from the glass fiber core 120 to the cap body 140B thereby resulting in the discharged laser energy 106C having an elliptical beam profile, the molded plano convex reflective surface 130B focuses or causes the discharged laser energy 106C to converge in the X and Z directions, resulting in a smaller, elliptical beam profile 300B.

Figure 10A:
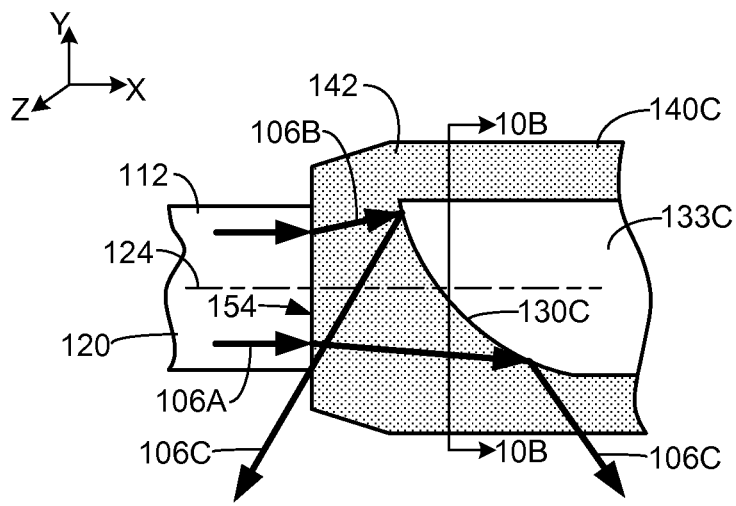
FIG. 10A is a simplified side cross-sectional view of a portion of a cap body in accordance with embodiments of the invention.
Figure 10B:
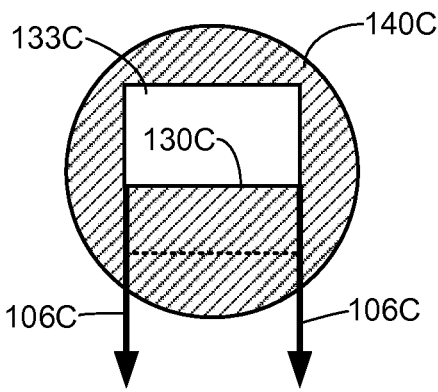
FIG. 10B is a front cross-sectional view of the cap body of FIG. 10A taken generally along line 10B-8B.
Figure 10C:
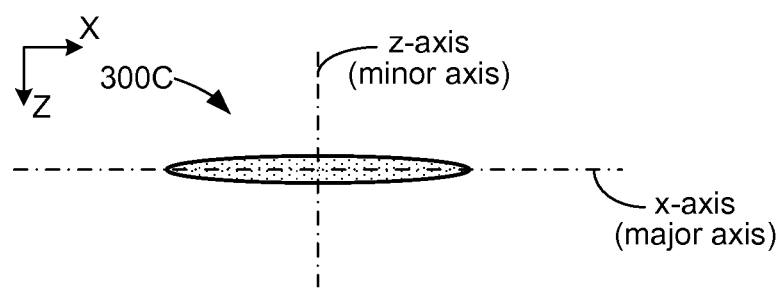
FIG. 10C depicts the beam profile generated by the cap body of FIGS. 10A and 10B.

FIG. 10A is a simplified side cross-sectional view of a portion of a cap body 140C and FIG. 10B is a front cross-sectional view of the cap body 140C of FIG. 10A taken generally along line 10B-10B, in accordance with embodiments of the invention. FIG. 10C depicts the beam profile 300C generated by the embodiment of the cap body 140C depicted in FIGS. 10A and 10B. The cap body 140C of FIGS. 10A and 10B includes a molded cylindrical plano concave reflective surface 130C. The molded cylindrical plano concave surface 130C expands or diverges the discharged laser energy 106C in only a single direction, which is the X direction in the figures and which is aligned with the central axis 124, resulting in the discharged laser energy 106C having an elongated elliptical (line-like) profile 300C as depicted in FIG. 10C. Thus, the molded cylindrical plano concave (concave relative to the cavity 133C) reflective surface 130C can be used to further expand the discharged laser energy 106C along the major axis of the ellipse forming an elongated, elliptical laser beam profile 300C where the major axis of the ellipse is aligned with the central axis 124 of the optical fiber 112. The radius of curvature of the molded cylindrical plano concave reflective surface 130C can be designed to control the amount that the discharged laser energy 106C expands/diverges along the major axis of the ellipse. Accordingly, laser beam profiles 300C can be generated in the form of an ellipse with a diameter along the major axis that is much greater than the diameter of the ellipse along the minor axis resulting in a large, long, narrow ellipse (line like), or with a diameter along the major axis that is closer to the diameter of the ellipse along the minor axis resulting in a shorter, wider ellipse (less line like). Thus, in this embodiment, the radius of curvature of the molded cylindrical plano concave reflective surface 130C controls the linearity of the discharged laser energy 106C.

Figure 11A:
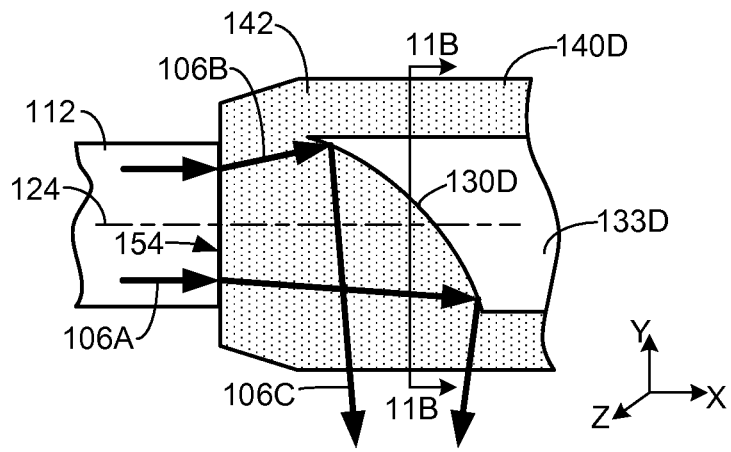
FIG. 11A is a simplified side cross-sectional view of a portion of a cap body in accordance with embodiments of the invention.
Figure 11B:
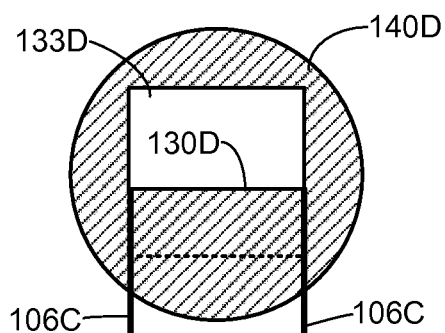
FIG. 11B is a front cross-sectional view of the cap body of FIG. 1A taken generally along line 11B-11B.
Figure 11C:
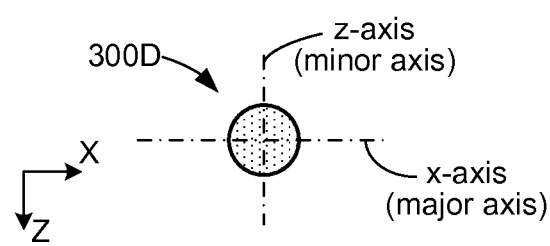
FIG. 11C depicts the beam profile generated by the cap body of FIGS. 11A and 11B.

FIG. 11A is a simplified side cross-sectional view of a portion of a cap body 140D and FIG. 11B is a front cross-sectional view of the cap body 140D of FIG. 11A taken generally along line 11B-11B, in accordance with embodiments of the invention. FIG. 11C depicts the beam profile 300D generated by the embodiment of the cap body 140D depicted in FIGS. 11A and 11B. The cap body 140D of FIGS. 11A and 11B includes a molded cylindrical plano convex reflective surface 130D. The cylindrical plano convex reflective surface 130D focuses the discharged laser energy 106C in only a single direction, which is the X direction in the figures and which is aligned with the central axis 124, resulting in the discharged laser energy 106C having a round profile 300D as depicted in FIG. 11C. Thus, the molded cylindrical plano convex (convex relative to the cavity 133D) reflective surface 130D can be used to focus the discharged laser energy 106C along the major axis of the ellipse in order to generate a round laser beam profile 300D. In addition, the radius of curvature of the molded cylindrical plano convex reflective surface 130D can be designed to control the degree that the discharged laser energy 106C is focused or converges along the major axis of the ellipse. Accordingly, laser beam profiles can be generated in the form of an ellipse with a diameter along the major axis that is similar to the diameter of the ellipse along the minor axis resulting in either a less-elliptical-like discharged laser energy 106C beam profile or a circular discharged laser energy 106C beam profile 300D.

Because (1) the molded plano concave reflective surfaces expand or diverge the discharged laser energy 106C and (2) the molded plano convex reflective surfaces focus or converge the discharged laser energy 106C, laser beam profiles generated by the molded plano concave reflective surfaces (FIGS. 8 and 10) are larger than the laser beam profiles generated by the molded plano convex reflective surfaces (FIGS. 9 and 11). The more focused discharged laser energy 106C of the smaller beam profiles of FIGS. 9 and 11 will have a higher energy density than the larger beam profiles of FIGS. 8 and 10, and may be more suitable for cutting tissue, fracturing kidney or bladder stones, or performing other laser treatments requiring a highly focused laser beam, for example.

In some embodiments, in order to generate a circular beam profile for the discharged laser energy 106C, the expansion or divergence of the laser energy 106B that occurs due to refraction from the change in medium from the glass fiber core 120 to the cap body 140 must be addressed. This expansion of laser energy 106B can be counteracted by designing a laser fiber 102 with an elliptically-shaped glass core and orienting the major axis of the elliptically-shaped glass core such that it is substantially perpendicular to the direction that the laser energy 106B expands in FIG. 3, i.e., substantially perpendicular to the Y direction. Thus, the elliptical beam profile that exits the elliptically-shaped glass core will be expanded along its minor axis, which is aligned with the Y direction in FIG. 3, due to refraction from the change in medium from the glass fiber core 120 to the cap body 140, thereby resulting in the discharged laser energy 106C having a more circular beam profile. Elliptical glass fiber cores can be designed to correspond to a planar molded reflective surface 130 of FIG. 3 such that it produces a circular discharged beam profile or a single elliptical glass fiber core can be designed and then multiple cap bodies 140 with different molded plano cylindrical concave reflective surfaces can be designed for use with the single elliptical glass fiber core to control the circularity and size of the discharged laser energy 106C beam profile.

While the exemplary molded reflective surfaces 130 have been described with reference to the cap body 140 of the laser fiber 102A, it is understood that these embodiments of the molded reflective surface 130 also apply to the laser fiber 102B. In addition, although embodiments of the cavities 133A-133D in FIGS. 8-11 have been depicted as having either a circular or rectangular cross-sectional shape, cavities 133A-133D can be molded to have any cross-sectional shape, i.e., circular, rectangular, elliptical, square, etc., for example.

Figure 12:
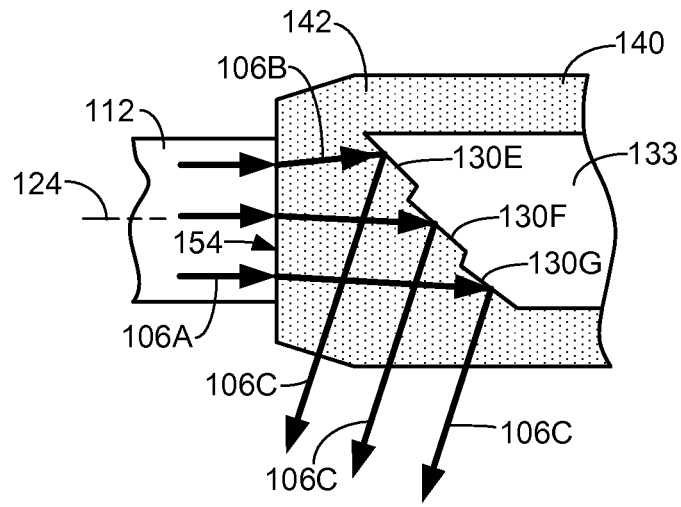
FIG. 12 is a simplified side cross-sectional view of a portion of a cap body in accordance with embodiments of the invention.

In some embodiments, the molded reflective surface 130 is configured to discharge output laser energy 106C in the form of a collimated laser beam. In some embodiments, the collimation of the laser energy 106B is achieved by two or more stepped surfaces formed in the molded reflective surface 130, such as stepped surfaces 130E-G, as shown in FIG. 12, which is a simplified side cross-sectional view of the cap body 140 in accordance with embodiments of the invention. In some embodiments, each of the stepped surfaces 130E-G is oriented at a different angle relative to the central axis 124 to compensate for the divergent laser energy 106B discharged from the optical fiber 112. The angles of the stepped surfaces 130E-G are selected to reflect the laser energy 106B in a manner that the discharged laser energy 106C is a substantially collimated laser beam.

Although the present invention has been described with reference to preferred embodiments, workers skilled in the art will recognize that changes may be made in form and detail without departing from the spirit and scope of the invention.

What is claimed is:

1. A side-fire laser fiber comprising:
   an optical fiber having a distal end and a distal facing surface at the distal end; and
   a fiber cap having a proximal end and a proximal facing surface at the proximal end, the fiber cap being coupled to the distal end of the optical fiber via a non-fused connection, and the fiber cap comprising a molded reflective surface and a sealed cavity, wherein the distal facing surface at the distal end of the optical fiber is flush against the proximal facing surface at the proximal end of the fiber cap;
   wherein:
   the molded reflective surface defines a wall of the cavity; and
   laser energy discharged from the distal end along a central axis of the optical fiber is reflected off the molded reflective surface in a direction that is transverse to the central axis.

2. The laser fiber of claim 1, wherein laser energy reflected off the molded reflective surface is discharged through a wall of the fiber cap.

3. The laser fiber of claim 1, wherein the cavity is filled with air.

4. The laser fiber according to claim 1, wherein laser energy discharged from the distal end of the optical fiber has a cross-sectional area, measured in a plane that is perpendicular to the central axis, that expands with distance from the distal end of the optical fiber along the central axis.

5. The laser fiber according to claim 1, wherein the reflective surface is curved in a plane extending at least one of parallel or perpendicular to the central axis.

6. The laser fiber according to claim 1, wherein the molded reflective surface comprises stepped surfaces, wherein each stepped surface is at a unique angle to the central axis.

7. The laser fiber according to claim 1, wherein the fiber cap includes a main body that defines the molded reflective surface and an opening to the cavity, and a cover member attached to the main body that seals the opening.

8. A laser fiber according to claim 1, wherein a portion of the cavity extends between the distal end of the optical fiber and the molded reflective surface.

9. The laser fiber according to claim 8, wherein the fiber cap includes a main body having a proximal end attached to the optical fiber and a distal end having an opening to the cavity, and a cover member attached to the main body that seals the cavity and supports the molded reflective surface.

10. The laser fiber according to claim 9, wherein portions of the main body surrounding the cavity include a highly reflective coating.

11. The laser fiber according to claim 9, wherein the main body includes a distal surface that is oriented at an oblique angle to the central axis, and the cover member is attached to the distal surface.

12. The laser fiber according to claim 1, wherein the molded reflective surface is selected from the group consisting of a molded spherical piano concave reflective surface, molded spherical piano convex reflective surface, a molded cylindrical piano concave reflective surface and a molded cylindrical piano convex reflective surface.

13. A side-fire laser fiber comprising:
    an optical fiber having a distal end and an exterior surface, the optical fiber including cladding on at least a portion of the exterior surface;
    a molded glass cap attached to the distal end of the optical fiber and comprising:
        a proximal end;
        a distal end;
        a total internal reflection surface; and
        an internal cavity formed between the proximal end and distal end, wherein the internal cavity:
            (i) is defined by the total internal reflection surface adjacent the proximal end of the molded glass cap, wherein the total internal reflection surface is spaced apart from the distal end of the optical fiber;
            (ii) is sealed at the distal end of the molded glass cap with a biocompatible material attached to the molded glass cap; and
            (iii) is filled with air; and
    a metal cap portion attached to the exterior surface of the optical fiber adjacent the distal end of the optical fiber, the metal cap portion comprising:
        a proximal end;
        a distal end;
        at least one irrigation opening to allow an irrigant to flow from an exterior of the metal cap portion to an interior of the metal cap portion and around at least a portion of the molded glass cap; and
        a side port to allow transmission of laser energy reflected off the total internal reflection surface of the molded glass cap, wherein:
    the proximal end of molded glass cap is attached to the distal end of the optical fiber via a non-fused connection;
    the distal end of the metal cap portion is attached to the distal end of the molded glass cap; and
    the proximal end of the metal cap portion is attached to the cladding on the distal end of the optical fiber.

14. The laser fiber according to claim 13, wherein the proximal end of the molded glass cap is flush with the distal end of the optical fiber.

15. The laser fiber according to claim 13, wherein the total internal reflection surface is selected from the group consisting of a spherical piano concave reflective surface, spherical piano convex reflective surface, a cylindrical piano concave reflective surface and a cylindrical piano convex reflective surface.

16. A side-fire laser fiber comprising:
    an optical fiber having a distal end and an exterior surface, the optical fiber including cladding on at least a portion of the exterior surface;
    a cap of a biocompatible material attached to the distal end of the optical fiber via a non-fused connection and comprising:
        a proximal end;
        a distal end;
        a total internal reflection surface; and
        an internal cavity formed between the proximal end and distal end, wherein the internal cavity:
            (i) is sealed at the distal end of the cap with a cover member;
            (ii) is sealed at the proximal end by the total internal reflection surface; and
            (iii) is filled with air,
    wherein the total internal reflection surface is distal of a distalmost end of the optical fiber.

17. The laser fiber according to claim 16, further comprising a metal cap having a proximal end attached to the distal end of the optical fiber, wherein at least a portion of the fiber cap is received within a distal end of the metal cap.

18. The laser fiber according to claim 17, wherein the distal end of the metal cap includes a side port in a wall of the metal cap through which the laser energy is discharged.

19. The laser fiber according to claim 18, wherein:
    the laser fiber further comprises a fluid conduit and fluid channels between the metal cap and the fiber cap;
    the optical fiber is within the fluid conduit; and
    fluid delivered through the fluid conduit travels through the fluid channels and out the side port of the metal cap.

20. The laser fiber according to claim 19, further comprising a seal between a distal end of the fluid conduit and the metal cap.

* * * * *